US007009057B2

(12) United States Patent
Halama et al.

(10) Patent No.: US 7,009,057 B2
(45) Date of Patent: Mar. 7, 2006

(54) METHOD FOR OBTAINING PIOGLITAZONE AS AN ANTIDIABETIC AGENT

(75) Inventors: Aleš Halama, Pardubice (CZ); Ludmila Hejtmánková, Prelouc (CZ); Petr Lustig, Pardubice (CZ); Jindřich Richter, Pardubice (CZ); Lucie Sršňová, Chrudim (CZ); Josef Jirman, Pardubice (CZ)

(73) Assignee: Zentiva A.S., Praha 10 (CZ)

( * ) Notice: Subject to any disclaimer, the term of this patent is extended or adjusted under 35 U.S.C. 154(b) by 84 days.

(21) Appl. No.: 10/475,099

(22) PCT Filed: Apr. 25, 2002

(86) PCT No.: PCT/CZ02/00024

§ 371 (c)(1),
(2), (4) Date: Oct. 27, 2003

(87) PCT Pub. No.: WO02/088120

PCT Pub. Date: Jul. 11, 2002

(65) Prior Publication Data

US 2005/0043360 A1    Feb. 24, 2005

(30) Foreign Application Priority Data

Apr. 26, 2001 (CZ) ................... 2001-1501
Apr. 26, 2001 (CZ) ................... 2001-1502

(51) Int. Cl.
C07D 417/12 (2006.01)

(52) U.S. Cl. .................. 546/269.7
(58) Field of Classification Search .............. 546/269.7
See application file for complete search history.

(56) References Cited

U.S. PATENT DOCUMENTS

2001/0008898 A1    7/2001    Tomiyama et al.

FOREIGN PATENT DOCUMENTS

| EP | 0 067 718 | 12/1982 |
| EP | 0 193 256 | 9/1986 |
| EP | 0 816 340 | 1/1998 |
| JP | 62 205054 | 9/1987 |

Primary Examiner—Patricia L. Morris

(74) Attorney, Agent, or Firm—Oblon, Spivak, McClelland, Maier & Neustadt, P.C.

(57) ABSTRACT

A method for obtaining antidiabetic of formula (I), wherein the method comprises condensing of a 4-derivatized phenol or phenolate of general formula (II), wherein R is an amino group-containing organic residue, selected from the group comprising a residue of the following formula $—NHR^3$, wherein $R^3$ is hydrogen or a protecting group, which is removed before further treatment, and a residue of general formula (A), wherein $R^b$ represents a carboxy group either in the free acid form or in the form of a salt or ester or another functional derivative or the nitrile group CN, and M represents a hydrogen or alkali metal atom, with a pyridine base of general formula (III, wherein Z is a leaving group other than a halogen, wherein, before or after carrying out the condensation, the following operations are carried out: (a) diazotizing the amino group present in organic residue R; (b) converting the diazotised residue R into a derivative of 2-halopropionate or 2-halopropionitrile of formula (B), wherein $R^b$ is as defined above and X is a halogen; (c) cyclizing the derivative of 2-halopropionate or 2-halopropionitrile with thiourea; (d) hydrolysing the resulting imine thus giving pioglitazone of formula (I)

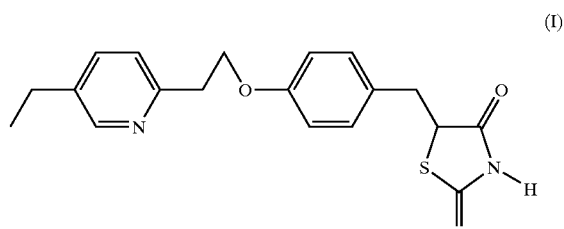

(I)

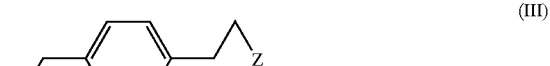

(III)

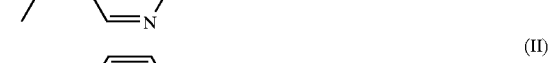

(II)

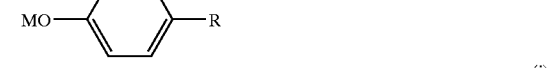

(i)

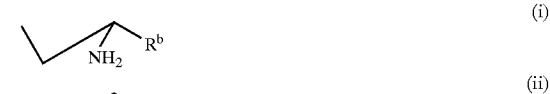

(ii)

15 Claims, No Drawings

METHOD FOR OBTAINING PIOGLITAZONE AS AN ANTIDIABETIC AGENT

TECHNICAL FIELD

The present invention relates to a method of obtaining an intermediate, useful for the production of (+/−)-5-[[4-[2-(5-ethyl-2-pyridyl)ethoxy]phenyl]methyl]-2,4-thiazolidinedione (termed pioglitazone hereinafter) of formula I

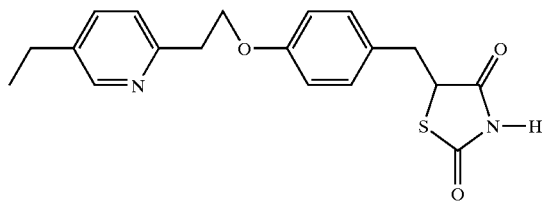

(I)

Pioglitazone belongs to the thiazolidinedione group of antidiabetics. This compound and its antidiabetic properties were described in EP 193 256. Later it was found that its antidiabetic effect consists in reducing insulin resistance, thereby improving glucose availability without increasing insulin secretion, unlike most other antidiabetics. For these extraordinary characteristics this product is of great importance for the treatment of non-insulin dependent diabetes mellitus. Combining with insulin or other antidiabetics can further increase its effect.

BACKGROUND ART

Synthesis of thiazolidinediones has been described in EP 177 353. Namely the preparation of compounds of formula VII

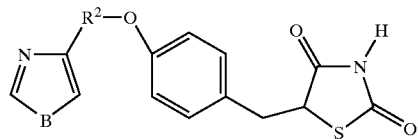

(VII)

wherein B is an oxygen or sulfur atom, $R^2$ is an alkyl, acyl or hydroxyalkyl, is described by reacting of a compound of formula VIII

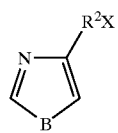

(VIII)

wherein X is a halogen,
and a phenolthiazolidinedione of formula VI

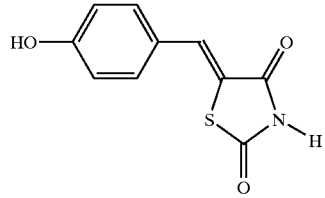

(VI)

The reactions are carried out in alkaline environment in organic solvents (e.g., dimethylformamide).

The method as described in EP 177 353 cannot be simply used for the synthesis of pioglitazone since in reacting 5-ethyl-2-pyridyl-ethylhalide with an appropriate phenol in an alkaline medium elimination reaction resulting in vinyl pyridine will prevail.

Therefore EP 193 256 discloses another reaction, which can be described by the following scheme

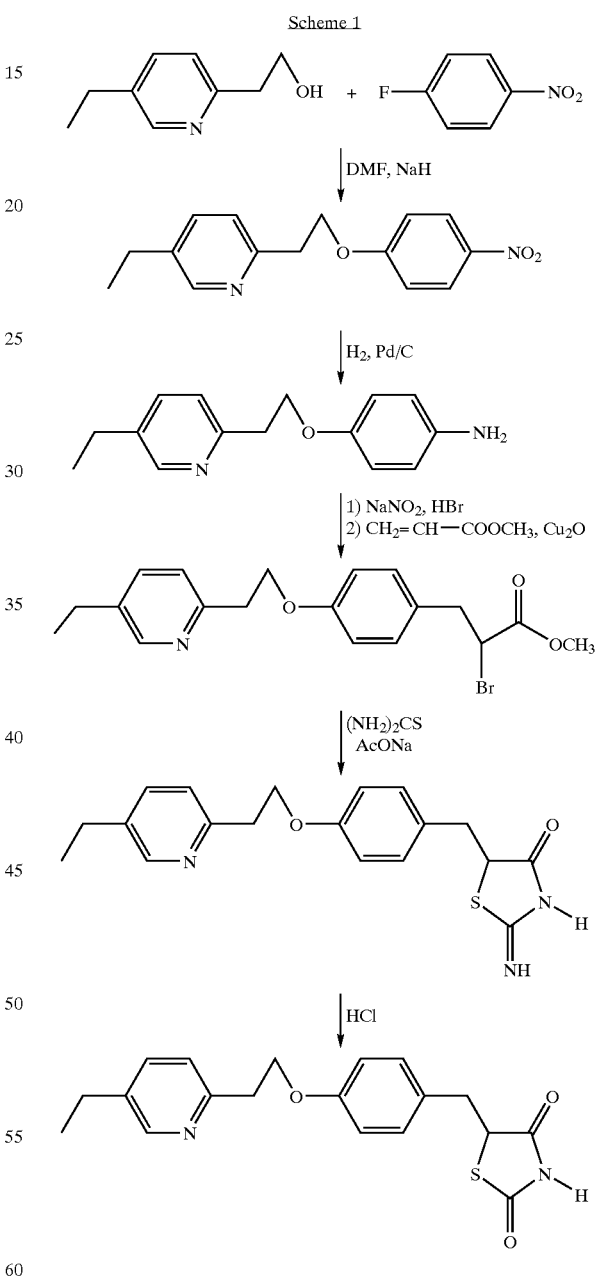

A major drawback of this method is non-standard course of the reduction of the nitro group on palladium (reaction time is 3 hours up to several days), which is apparently dependent on the contents of impurities in the starting compound and in the solvent. The impurities apparently cause poisoning of the catalyst; therefore additional catalyst has to be gradually added. Longer reaction time results in formation of larger amounts of impurities and lower yields.

Further methods how to solve this problem have been elaborated in EP 257 78 1, in Chem. Pharm. Bull. 39(6) 1440–1445 (1991) and in EP 506 273 and EP 816 340. A common feature of all these methods is the reaction of a compound of formula III

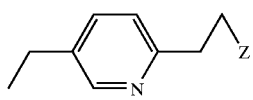

(III)

wherein Z is a leaving group of general formula $R^3SO_3$ wherein $R^3$ is an alkyl or aryl, with an alkali metal p-hydroxybenzaldehyde or p-formylphenolate, i.e. with a compound of general formula IX

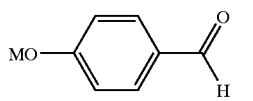

(IX)

wherein M can represent an alkali metal or hydrogen.

The product of formula X

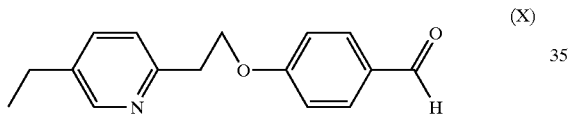

(X)

further reacts with thiazolidinedione yielding a benzylidene compound of formula XI

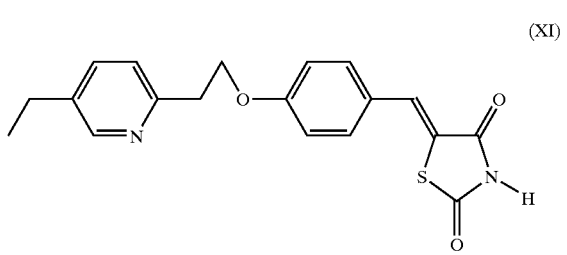

(XI)

which is converted to pioglitazone (formula I) by reducing on palladium.

The methods in the above-cited patents differ especially in the media in which reaction of the compound IX with the compound III is carried out. In EP 257 781 and in Chem. Pharm. Bull. 39(6) 1440–1445 (1991) reactions in a heterogeneous environment methylene chloride-water in the presence of a phase transfer catalyst have been described. In this embodiment, the main problem lies in the phase transfer. In the embodiment according to EP 506 273 an alkali metal 4-formylphenolate was first isolated and used as the starting material in the subsequent steps of the preparation. The reaction occurred in an anhydrous environment, preferably in ethanol. In EP 816 340 reaction in an anhydrous solvent mixture containing a low-molecular alcohol with another organic solvent (for example toluene) is described.

A drawback of the above-described methods is necessity of pressure reduction of the double bond of compound XI, i.e. 5-(4-(2-(5-ethyl-2-pyridyl)ethoxy)benzylidene)-2,4-thiazolidinedione. The following methods are known:

According to EP 257 781 reduction is carried out with hydrogen under catalysis with rather expensive palladium at the gauge pressure of 50 kg/cm² and the temperature of 50° C. with the yield of 64%.

According to EP 506 273 at the gauge pressure of 100 kg/cm² and the temperature of 110° C. the yield is 72%. Higher yields can be obtained at the expense of increasing the pressure, which entails higher demands for safety of the reaction. Higher temperatures bring about generally higher risk of formation of undesired products.

An attempt at solving these problems has been given in the patent application WO 93/13095. It relates to reduction with sodium tetrahydroborate catalysed with cobalt chloride.

DISCLOSURE OF INVENTION

The solution in accordance with the present invention involves condensing 4-derivatized phenol or phenolate with a pyridine base of general formula III

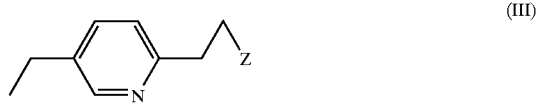

(III)

wherein Z is a leaving group other than a halogen, the starting compound of formula II

(II)

wherein R is an amino group-containing organic residue, selected from the group comprising a residue of general formula —NHR$^a$ wherein R$^a$ is hydrogen or a protecting group, which is removed before further treatment, and a residue of the general formula

wherein R$^b$ represents a carboxy group either in the free acid form or in the form of a salt or ester of another functional derivative of the nitrile group CN, and M represents a hydrogen atom or an alkali metal, being subjected, before or after carrying out the condensation, to the following operations:

a. diazotizing the amino group present in organic residue R b. converting the diazotized residue R into a derivative of 2-halopropionate or 2-halopropionitrile of formula

wherein $R^b$ is as defined above and X is a halogen c. cyclizing the derivative of 2-halopropionate or 2-halopropionitrile with thiourea d. hydrolyzing the resulting imine thus giving thiazolidinedione cycle.

Diazotizing

Diazotizing is preformed from the bromohydride of the respective aniline derivative or amino acid by drop-by-drop adding a solution of sodium nitrite in water at about 5° C.

Converting into the halo derivative of general formula

is performed, depending of the type of the starting compound II, either directly in the course of diazotising in the presence of an excess of halide ions or by adding an acrylate or acrylonitrile and cuprous oxide to the solution of the completed diazonium salt.

Cyclizing with thiourea is carried out in ethanol at its boiling point with subsequent separation of the product.

The subsequent hydrolysis, resulting in formation of the thiazolidinedione cycle, is carried out with hydrochloric acid at its boiling point.

The condensation with 2-(5-ethyl-2-pyridyl)ethyl derivative itself is carried out in the presence of a base in the form of an alkali metal carbonate, hydroxide or hydride in an organic solvent or in a heterogeneous mixture of an organic solvent and water. The temperature when performed in an organic solvent ranges between 50 and 130° C. After the reaction is complete the solvent can be evaporated, or, if it is a high-boiling solvent, water is added to the mixture. The product is extracted with ethyl acetate.

If R is a residue of formula

—NHR$^a$ wherein $R^a$ is as defined above, then condensing of compounds II and III results in a compound of formula V

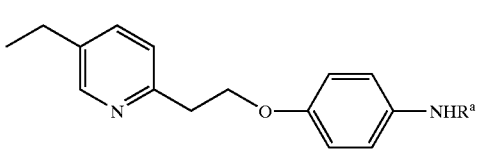

(V)

Where $R^a$ is a leaving group, then formula V represents a yet undisclosed compound. The selection of the leaving group $R^a$ is not essential for further procedure. It can be selected among the groups such as acyl, n-alkyloxycarbonyl, tert-butyloxycarbonyl, benzyloxycarbonyl, 9-fluorenylmethyloxycarbonyl, allyloxycarbonyl, 2-cyanoethoxycarbonyl, dimethylaminomethylenyl or hexa-2,4-dien-2,5-diyl.

Preferably, $R^a$ can be an acyl group derived from lower aliphatic acids ($C_1$ to $C_4$), such as acetyl, or from lower aromatic acids, such as benzoyl.

Degradation of the compound of formula V results in a compound of formula IV

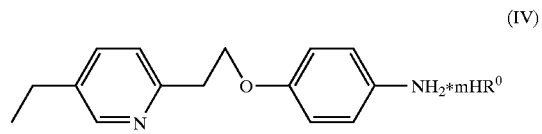

(IV)

wherein m stands for 0 (for a free amine) or 1 (for ammonium salt), $R^0$ is a mineral or organic acid residue such as a halogen, $HSO_4^-$, $NO_3^-$, $R^1COO-$ or $R^1SO_3-$, wherein $R^1$ represents hydrogen or a hydrocarbon residue, which can be advantageously used for the preparation of pioglitazone.

The hydrolysis itself is carried out with a mineral or organic acid of general formula $HR^0$ or with a base.

In case of basic hydrolysis carried out, e.g., from a mixture of potassium hydroxide and ethanol at the boiling temperature, compound IV represents 4-(2-(5-ethyl-2-pyridyl)ethoxy)aniline, i.e. the free base (m is 0).

In case of acidic hydrolysis for example haloacids such as hydrochloric acid can be used; compound IV, formed during the reaction, represents 4-(2-(5-ethyl-2-pyridyl)ethoxy) aniline hydrochloride, which, during isolation, is converted into the free base (m=0). From the point of view of the subsequent step of pioglitazone synthesis (diazotizing), hydrobromic acid is especially preferable for hydrolysis of compound of formula V, when $R^0$ represents Br and the product of formula IV, 4-(2-(5-ethyl-2-pyridyl)ethoxy) aniline hydrobromide, need not to be isolated. Oxygen-containing mineral acids such as sulphuric acid can also be used in the hydrolysis. Useful organic acids include alkyl- or arylsulfonic acids (such as methanesulfonic acid). Numerous carboxylic acids such as formic or acetic acids can be used for the hydrolysis.

The compound of formula IV is further treated in a known manner, i.e. by diazotizing, Meerwein reaction, cyclizing with thiourea and hydrolysing the imine. This method has been described in EP 193 256 and is here depicted in Scheme 1.

In case of the most common protective group, wherein $R^a$ is acetyl, its decomposition is carried out using a mixture, preferably a mixture of concentrated hydrobromic acid with ethanol in the volume ratio 1:3.

If R is a residue of formula

wherein $R^b$ is carboxyl or nitrile, it is preferable to effect the steps of diazotizing, converting into the halo residue, cyclizing and hydrolyzing prior to condensation itself.

In thus case an intermediate of formula VI

VI is formed, with which the condensation is subsequently carried out. In this case the starting compound can be the amino acid tyrosine, an inexpensive natural source of formula Condensation of intermediate VI with base III can in this case be made in an organic polar solvent such as dimethylformamide or dimethylsulfoxide. The reaction temperature is selected in dependence of the base employed in the range of from 70 to 130° C. The reaction time ranges, again in connection with the selected base, between 0.5 and 3 hours. In a usual embodiment, after the reaction is complete the reaction mixture is quenched with water and the product is extracted, usually with acetate.

The complete synthesis of pioglitazone in the above-described special case can be schematically depicted:

Scheme 2

If R is a protected amine of formula —$NHR^a$, the most preferable composition is the case when $R^a$ is acetyl, and the compound of formula II is widely used paracetamol.

The condensation in this case is preferably carried out in ethanol at 50° C. After the reaction is complete ethanol is evaporated and the product extracted with ethyl acetate.

A complete scheme of this preferable procedure with reference to the respective working examples is depicted in Scheme 3:

Scheme 3

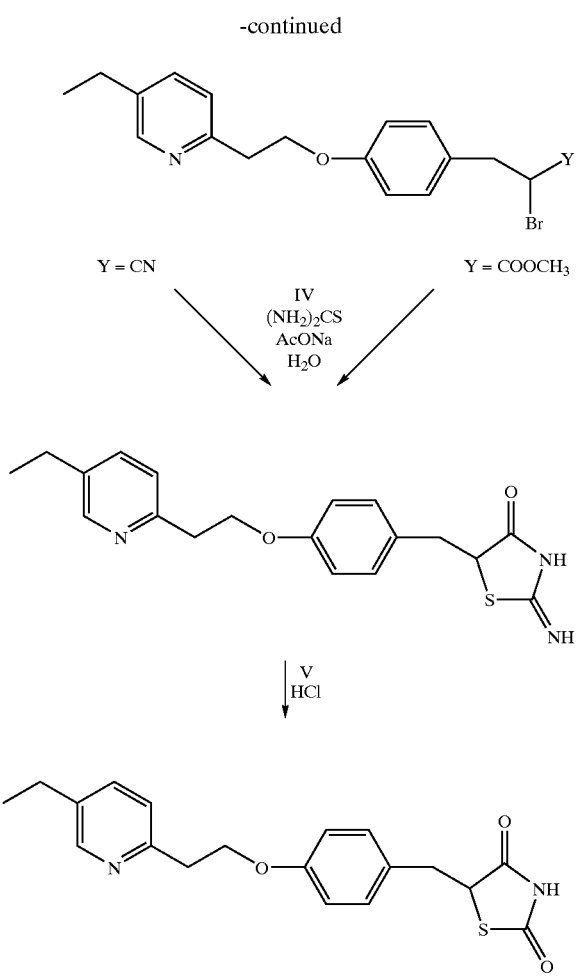

EXAMPLES

The following examples will further illustrate the present invention.

Reference Example

Preparation of Pioglitazone According to EP 193 256 a) Preparation of 4-(2-(5-ethyl-2-pyridyl)ethoxy)nitrobenzene

To a solution of 2-(5-ethyl-2-pyridyl)ethanol (12 g) and 4-fluoronitrobenzene (11.2 g) in dimethylformamide (80 ml) sodium hydride (3.9 g) is added portionwise under ice cooling. This mixture is agitated under ice cooling for one hour, at room temperature for thirty minutes, poured into ice water and extracted with ethyl acetate. Drying the organic layer and evaporating the solvent gives a yellow solid (4-(2-(5-ethyl-2-pyridyl)ethoxy)nitrobenzene, 21.4 g, 98.2%). Recrystallizing from a mixture of ether and hexane yields pale yellow crystals (m.p. 45–47° C.). NMR δ (ppm) in CDCl$_3$: 1.25 (3H, t, J=7.6), 2.65 (2H, q, J=7.6), 3.28 (2H, t, J=6.7), 4.47 (2H, t, J=6.7), 6.95 (2H, m), 7.19 (1H, d, J=7.9), 7.49 (1H, dd, J=2.4; 8.0), 8.17 (2H, m), 8.41 (1H, d, J=2.2).

b) Preparation of 4-(2-(5-ethyl-2-pyridyl)ethoxy)aniline

A solution of 4-(2-(5-ethyl-2-pyridyl)ethoxy)nitrobenzene (23 g) in methanol is hydrogenated under atmospheric pressure in the presence of 10% Pd on carbon (50% humid, 2.5 g). The catalyst is removed by filtering. Distilling the solvent off under reduced pressure gives 4-(2-(5-ethyl-2-pyridyl)ethoxy)aniline as crude oil (20 g, 98%).

c) Preparation of methyl 2-bromo-3-(4-(2-(5-ethyl-2-pyridyl)ethoxy)phenyl)propionate To a solution of 4-(2-(5-ethyl-2-pyridyl)ethoxy)aniline (20.4 g) in a mixture of methanol (70 ml) and acetone (180 ml) 47% hydrobromic acid (36 ml) is added. The mixture is cooled. A solution of sodium nitrite (6.12 g) in water (18 ml) is added dropwise at 0 to 5° C. The mixture is agitated for another twenty minutes at this temperature, then methyl acrylate (43.2 ml) is added and the temperature is elevated to 38° C. To this mixture cuprous oxide (0.72 g) is added in small portions under mixing. The reaction mixture is mixed as long as nitrogen is released. Then it is concentrated under reduced pressure, the concentrate is alkalified by addition of a concentrated ammonia solution (36 ml) and extracted into ethyl acetate. The organic layer is washed with water and dried over sodium sulfate. Concentrating gives methyl 2-bromo-3-(4-(2-(5-ethyl-2-pyridyl)ethoxy)phenyl)propionate as crude oil (28.4 g; 86.2%). NMR δ (ppm) in CDCl$_3$: 1.21 (3H, t, J=7), 2.60 (2H, q, J=7), 3.0–3.6 (4H, m), 3.66 (3H, m), 4.30 (2H, t, J=7), 4.3 (1H, m), 6.7–7.5 (6H, m), 8.35 (1H, d, J=2)

d) Preparation of 5-(4-(2-(5-ethyl-2-pyridyl)ethoxy)benzyl)-2-imino-4-thiazolidinone A mixture of methyl 2-bromo-3-(4-(2-(5-ethyl-2-pyridyl)ethoxy)phenyl)propionate (28.4 g), thiourea (5.5 g), sodium acetate (6 g) and ethanol (200 ml) is heated to reflux under heating for three hours. The mixture is concentrated and the concentrate is neutralized with saturated solution of sodium hydrogencarbonate. Adding water (80 ml) and ether (40 ml) precipitates a solid from the mixture. Filtering off gives beige-coloured crystalline 5-(4-(2-(5-ethyl-2-pyridyl)ethoxy)benzyl)-2-imino-4-thiazolidinone (21.4 g; 85.9%; m.p. 178–182° C.). NMR δ (ppm) in CDCl$_3$: 1.2 (3H, t, J=7.6), 2.61 (2H, q, J=7.6), 2.85 (1H, dd, J=9.4; 14.3), 3.14 (2H, t, J=6.7), 3.31 (1H, dd, J=4.1; 14.2), 4.31 (2H, t, J=6.7), 4.52 (1H, dd J=4.1; 9.4), 6.84 (2H, m), 7.14 (2H, m), 7.27 (1H, 6d, J=7.9), 7.57 (1H, 6dd, J=2.3; 7.9), 8.38 (1H, 6d J=2.2), 8.7 (2H, 6s).

e) Preparation of 5-(4-(2-(5-ethyl-2-pyridyl)ethoxy)benzyl)-2,4-thiazolidindione A solution of 5-(4-(2-(5-ethyl-2-pyridyl)ethoxy)benzyl)-2-imino-4-thiazolidinone (21.4 g) in 2M hydrochloric acid (200 ml) is heated to reflux for six hours, then concentrated under reduced pressure. The evaporation residue is neutralized with saturated solution of sodium hydrogencarbonate, the crude product is filtered from the mixture. Recrystallizing from a mixture of dimethylformamide and water gives crystalline 5-(4-(2-(5-ethyl-2-pyridyl)ethoxy)benzyl)-2,4-thiazolidinedione (10.6 g; 56.1%; m.p. 170–173° C.). NMR δ (ppm) in CDCl$_3$: 1.24 (3H, t, J=7.6), 2.64 (2H, q, J=7.6), 3.04 (1H, dd, J=9.4; 14.3), 3.21 (2H, t, J=6.6), 3.39 (1H, dd, J=4.0; 14.2), 4.33 (2H, t, J=6.6), 4.48 (1H, dd, J=4.0;9.3), 6.83 (2H, m), 7.12 (2H, m), 7.27 (1H, d, J=8.0), 7.50 (1H, dd, J=2.3; 8.0), 8.37 (1H, d, J=1.9).

Example 1

Preparation of 4-(2-(5-ethyl-2-pyridyl)ethoxy)aniline

Preparation of 4-(2-(5-ethyl-2-pyridyl)ethoxy)acetanilide (Condensation—Two Different Starting Salts)

a) A mixture of 2-(5-ethyl-2-pyridyl)ethyl mesylate (3.64 g) and potassium 4-acetamidophenolate (3.32 g) in ethanol (18 ml) is agitated at 60° C. for six hours. The mixture is concentrated and extracted with ethyl acetate and water. The organic layer is washed 3× with a 0.2M solution of sodium hydroxide and 2× with water and dried with sodium sulfate. Evaporating the solvent and washing the residue with ether gives crystalline 4-(2-(5-ethyl-2-pyridyl)ethoxy)acetanilide (2.32 g, 51.3%; m.p. 85–87° C.).

b) To a solution of 2-(5-ethyl-2-pyridyl)ethyltosylate (15.27 g) in ethanol (50 ml) a solution of potassium 4-acetamidophenolate (9.47 g) in ethanol (40 ml) is added at 50–60° C. during 1.5 hours. The reaction mixture is agitated at the same temperature for another six hours, concentrated and extracted with ethyl acetate (150 ml) and water. The organic layer is washed with a 0.2M solution of sodium hydroxide (4×100 ml) and water (2×100 ml) and dried over sodium sulfate. Evaporating the solvent and washing the residue with ether gives crystalline 4-(2-(5-ethyl-2-pyridyl)ethoxy)acetanilide (6 g, 42.3%, m.p. 85.5–87° C.).

Preparation of 4-(2-(5-ethyl-2-pyridyl)ethoxy)aniline (Three Different Modifications)

a) A solution of 4-(2-(5-ethyl-2-pyridyl)ethoxy)acetanilide (13 g) in a mixture of ethanol (80 ml) and concentrated hydrochloric acid (80 ml) is heated to reflux for 2.5 hours. The reaction mixture is neutralized with an aqueous solution of sodium hydroxide and extracted with ethyl acetate. The organic layer is washed with water and dried over magnesium sulfate. Evaporating ethyl acetate gives oily 4-(2-(5-ethyl-2-pyridyl)ethoxy)aniline (9.6 g, 88.1%).

b) A mixture of 4-(2-(5-ethyl-2-pyridyl)ethoxy)acetanilide (15.5 g), 4 M potassium hydroxide (150 ml) and ethanol (150 ml) is refluxed for 20 hrs and ethanol is evaporated. The mixture is extracted with ethyl acetate; the organic layer is washed with water and dried over sodium sulfate. Evaporating the solvent gives an oily product, 4-(2-(5-ethyl-2-pyridyl)ethoxy)aniline (11.03 g; 80%)

c) To a solution of 4-(2-(5-ethyl-2-pyridyl)ethoxy)acetanilide (6 g) in ethanol (100 ml) concentrated hydrobromic acid (36 ml) is added. The mixture is heated t reflux for 4 hrs. After evaporating ethanol the residual mixture is used for the next synthetic step without further isolation.

Example 2

4-(2-(5-ethyl-2-pyridyl)ethoxy)aniline

Preparation of 4-(2-(5-ethyl-2-pyridyl)ethoxy)acetanilide

To a solution of 2-(5-ethyl-2-pyridyl)ethyl mesylate (1.7 g) and benzyltributylammonium chloride (0.5 g) in dichloromethane (10 ml) a solution of 4-hydroxyacetanilide (1.2 g) and potassium carbonate (1.1 g) in water (10 ml) is added. After agitating for 9 hours and heating to 75° C. the organic layer is separated, washed with water and dried over sodium sulfate. Evaporating the solvent and washing the residue with ether gives crystalline 4-(2-(5-ethyl-2-pyridyl)ethoxy)acetanilide (1.15 g; 54.8%; 82–85° C.).

Preparation of 4-(2-(5-ethyl-2-pyridyl)ethoxy)aniline 4-(2-(5-ethyl-2-pyridyl)ethoxy)acetaniline is obtained by hydrolysing 4-(2-(5-ethyl-2-pyridyl)-ethoxy)acetanilide as described in Example 1.

Example 3

Preparation of 5-[[4-[2-(5-ethyl-2-pyridyl)ethoxy] phenyl]methyl]-2.4-thiazolidinedione (pioglitazone)

Preparation of 2-bromo-3-(4-hydroxyphenyl)-propionic acid

Tyrosine (20 g) is dissolved in HBr (100 ml, 48% diluted with 200 ml water). To the cooled solution $NaNO_2$ in 30 ml water is added dropwise. The product is extracted with ethyl acetate and after common treatment 2-bromo-3-(4-hydroxyphenyl)-propionic acid is obtained, which is used without purification for the next step.

Preparation of 5-(4-hydroxybenzyl)-1,3-thiazolidine-2,4-dione 2-bromo-3-(4-hydroxyphenyl)-propionic acid is refluxed in ethanol (150 ml) with thiourea (14.7 g) and sodium acetate (16.32 g). After 3.5 hrs the solvent is evaporated. The residue is mixed in water, filtered off and washed with ether. A product (17.15 g) having the melting point 180.5–183.6° C. is obtained.

The obtained 5-(4-hydroxybenzyl)-2-imino-1,3-thiazolidine-4-one (16 g) is dissolved in methoxyethanol (150 ml) and HCl (27 ml) is added. The reaction mixture is refluxed for 4 hours. After evaporating the solvent the residue is mixed with water. The product is extracted from water with ethyl acetate.

The product can be recrystallized from a mixture ethyl acetate-heptane. 9.5 g of 5-(4-hydroxybenzyl)-1,3-thiazolidine-2,4-dione having a melting point 150.9–152.5° C. is obtained.

Preparation of 5-[[4-[2-(5-ethyl-2-pyridyl)ethoxy] phenyl]methyl]-2,4-thiazolidinedione 0.5 g of 5-(4-hydroxybenzyl)-1,3-thiazolidine-2,4-dione is dissolved in ethanol (7 ml) with KOH (0.25 g) and mixed at room temperature for 2 hours. To the obtained salt 2-(5-ethyl-2-pyridyl)ethyl tosylate is added and the reaction mixture is refluxed for 5 hours. After cooling the precipitated salt is filtered off, pH is adjusted and the solvent is evaporated. The semi-solid residue is mixed in water and the solid portion of 5-[[4-[2-(5-ethyl-2-pyridyl) ethoxy]phenyl]methyl]-2.4-thiazolidinedione (0.18 g) is filtered off and recrystallized from the mixture DMF-water.

Example 4

Preparation of 5-[[4-[2-(5-ethyl-2-pyridyl)ethoxy] phenyl]methyl]-2,4-thiazolidinedione (pioglitazone)—Another Method Preparation of 2-bromo-3-[4-(2-(5-ethyl-2-pyridyl)ethoxy) fenyl]propionic acid nitrile To a solution of 4-(2-(5-ethyl-2-pyridyl)ethoxy)phenylammonium bromide (52.8 mmol) in hydrobromic acid (prepared by hydrolyzing 4-(2-(5-ethyl-2-pyridyl)ethoxy) acetanilide according to Example 1c) 25 ml of 48% hydrobromic acid, 50 ml of methanol, 100 ml of acetone are added and the mixture is cooled to 0° C. A solution of sodium nitrite (4.5 g) in water (10 ml) is added dropwise to the mixture at 0 to 5° C. The mixture is mixed at 5° C. for another 20 mins, then acrylonitrile (16.8 ml) is added and the temperature is elevated to 38° C. Cuprous oxide (0.5 g) is added in small portions. The mixture is agitated until release of nitrogen stops, then concentrated under reduced pressure, the concentrate is alkalified by adding an aqueous ammonia solution and extracted with ethyl acetate. The ethylacetate layer is washed with water and dried over sodium sulfate. Evaporating the solvent gives the nitrile of 2-bromo-3-[4-(2-(5-ethyl-2-pyridyl)ethoxy)phenyl]-propionic acid as crude oil (18.7 g, 99% of theory).

Preparation of 5-[4-(2-(5-ethyl-2-pyridyl)ethoxy)benzyl]-2-imino-4-thiazolidinone A mixture of 2-bromo-3-[4-(2-(5-ethyl-2-pyridyl)ethoxy) phenyl]propionic acid nitrile (18.7 g), thiourea (3.9 g), sodium acetate (4.2 g) and ethanol (110 ml) is heated to reflux for 6 hours, then it is concentrated under reduced pressure, ethyl acetate (30 ml) and saturated sodium hydrogen carbonate solution (100 ml) are added. The mixture is left to stand overnight, then filtered and the precipitated beige solid washed with ether to give 5-[4-(2-(5-ethyl-2-pyridyl)ethoxy)benzyl]-2-imino-4-thiazolidinone (11.2 g, 59% of theory).

5-[4-(2-(5-ethyl-2-pyridyl)ethoxy)benzyl]-2-imino-4-thiazolidinone is then treated in the same manner as in Example 3.

The invention claimed is:

1. A method for obtaining the antidiabetic of formula I

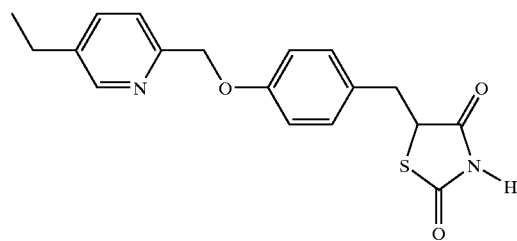
(I)

comprising
condensing a compound of formula III where Z is a leaving group with a compound of formula II where $R_1$ is a protecting group

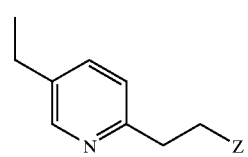
(III)

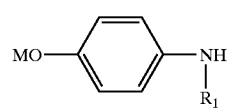
(II)

to form an ether of formula IV:

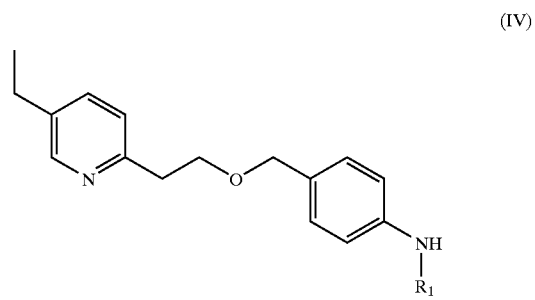
(IV)

removing protecting group $R_1$ from formula IV to form an aniline of formula V:

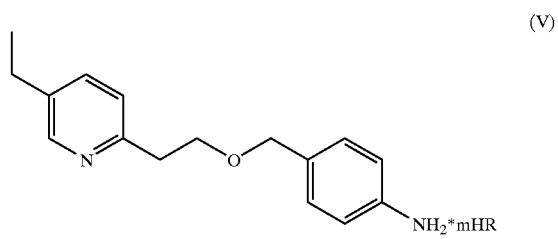
(V)

converting the aniline of formula V to a diazonium salt, reacting the diazonium salt with an olefin of formula VI where $R_2$ is an electron withdrawing group

(VI)

to form an alkyl halide of formula VII:

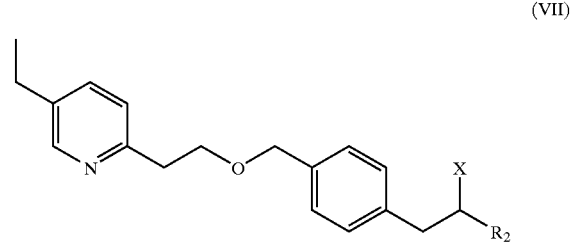
(VII)

reacting the alkyl halide of formula VII with thiourea to form an imine of formula VIII:

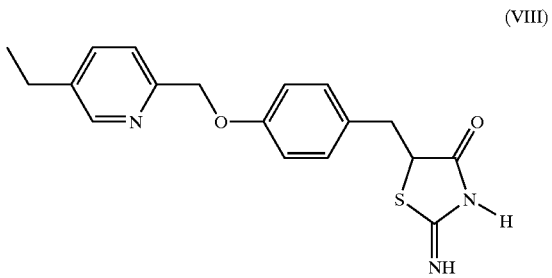
(VIII)

and,
hydrolyzing the imine of formula VIII to give the antidiabetic of formula I;

wherein
the leaving group Z is a radical of the formula

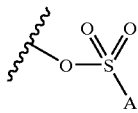

wherein A, which may be substituted or unsubstituted, is an aryl or an alkyl group;
wherein M is hydrogen or an alkali metal;
wherein the protecting group $R_1$ is selected from the group consisting of an acyl group derived from lower aliphatic acids ($C_1$–$C_4$), an acyl group derived from lower aromatic acids, n-alkyloxycarbonyl, tert-butyloxycarbonyl, benzyloxycarbonyl, 9-fluorenylmethyloxycarbonyl, alloxycarbonyl, 2-cyanoethoxycarbonyl, dimethylaminomethylenyl, and hexa-2,4-dien-2,5-diyl;
wherein m is 0 or 1;
wherein when m=1, R=Br;
wherein the electron withdrawing group $R_2$ is selected from the group consisting of a cyano group, a carboxylic acid, an ester, and the salt of a carboxylic acid;
and wherein X is a halogen atom.

2. The method of claim 1, wherein A is $CH_3$.

3. The method of claim 1, wherein A is a radical of the formula

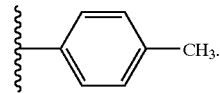

4. The method of claim 1, wherein M is hydrogen.
5. The method of claim 1, wherein M is potassium.
6. The method of claim 1, wherein $R_1$ is acetyl.

7. The method of claim 1, wherein $R_2$ is a radical of the formula

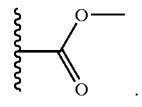

8. The method of claim 1, wherein $R_2$ is CN.
9. The method of claim 1, wherein X is Br.
10. The method of claim 1, wherein the condensing a compound of formula III where Z is a leaving group with a compound of formula II where $R_1$ is a protecting group is carried out in a heterogeneous mixture of an organic solvent and water in the presence of a phase transfer catalyst.
11. The method of claim 1, wherein protecting group $R_1$ is removed to form an aniline of formula V is accomplished by placing the ether of formula IV in an acidic environment.
12. The method of claim 1, wherein protecting group $R_1$ is removed to form an aniline of formula V is accomplished by placing the ether of formula IV in an alkaline environment.
13. The method of claim 1, wherein the converting the aniline of formula V to a diazonium salt comprises reagents comprising sodium nitrite and hydrobromic acid.
14. The method of claim 1, wherein the reacting the diazonium salt with an olefin of formula VI where $R_2$ is an electron withdrawing group to form an alkyl halide of formula VII comprises at least one reagent comprising cuprous oxide.
15. The method of claim 1, wherein the converting the aniline of formula V to a diazonium salt crude reaction product is, without isolation, reacted with with an olefin of formula VI where $R_2$ is an electron withdrawing group to form the alkyl halide of formula VII.

* * * * *

UNITED STATES PATENT AND TRADEMARK OFFICE
CERTIFICATE OF CORRECTION

PATENT NO. : 7,009,057 B2
DATED : March 7, 2006
INVENTOR(S) : Halama et al.

It is certified that error appears in the above-identified patent and that said Letters Patent is hereby corrected as shown below:

<u>Title page,</u>
Item [87], should read:
-- [87] PCT Pub. No.: WO02/088120
     PCT Pub. Date: Nov. 07, 2002 --.

Signed and Sealed this

Sixteenth Day of May, 2006

JON W. DUDAS
*Director of the United States Patent and Trademark Office*